(12) United States Patent
Xu et al.

(10) Patent No.: US 6,419,903 B1
(45) Date of Patent: Jul. 16, 2002

(54) BREATH FRESHENING FILM

(75) Inventors: Goufeng Xu, Princeton; Mel Reci, Pompton Lakes; Bernie L. Blackwell, Ringoes; Richard S. Robinson, Hillsborough; David B. Viscio, Monmouth Junction; John P. Curtis, Alpha, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/933,095

(22) Filed: Aug. 20, 2001

(51) Int. Cl.[7] .................. A61K 7/16; A61K 47/26; A61K 7/26
(52) U.S. Cl. .............. 424/49; 424/401; 424/435; 424/58
(58) Field of Search ............... 424/47–58, 401, 424/435, 49

(56) References Cited

U.S. PATENT DOCUMENTS

| | | | | |
|---|---|---|---|---|
| 4,448,789 A | * | 5/1984 | Yang | 426/5 |
| 4,569,852 A | * | 2/1986 | Yang | 426/534 |
| 4,576,826 A | * | 3/1986 | Liv et al. | 426/289 |
| 4,713,243 A | * | 12/1987 | Schiraldi et al. | 424/151 |
| 4,849,246 A | * | 7/1989 | Schmidt | 427/2 |
| 4,925,670 A | * | 5/1990 | Schmidt | 424/443 |
| 5,004,595 A | * | 4/1991 | Chervkuri et al. | 424/98 |
| 5,021,249 A | * | 6/1991 | Bvnick et al. | 426/96 |
| 5,284,659 A | * | 2/1994 | Chervkvri et al. | 424/441 |
| 5,354,551 A | * | 10/1994 | Schmidt | 424/401 |
| 5,603,971 A | * | 2/1997 | Porzio et al. | 426/96 |
| 5,726,161 A | * | 3/1998 | Whistler | 514/54 |
| 5,897,897 A | * | 4/1999 | Purzio et al. | 426/96 |
| 5,948,430 A | * | 9/1999 | Zerbe et al. | 424/435 |
| 6,174,514 B1 | * | 1/2001 | Chervkvri et al. | 424/48 |
| 6,177,096 B1 | * | 1/2001 | Zerbe et al. | 424/435 |
| 6,187,351 B1 | * | 2/2001 | Purzio et al. | 426/96 |
| 6,231,957 B1 | * | 5/2001 | Zerbe et al. | 428/220 |

FOREIGN PATENT DOCUMENTS

| | | | |
|---|---|---|---|
| DE | 36 30 603 | * | 3/1988 |
| EP | 0 219 762 | * | 10/1986 |
| WO | 00/18365 | * | 4/2000 |

* cited by examiner

*Primary Examiner*—Shep K. Rose
(74) *Attorney, Agent, or Firm*—Paul Shapiro

(57) ABSTRACT

A rapidly dissolvable orally consumable film composition for delivering breath freshening agents to the oral cavity wherein the composition is formed from a homogeneous mixture of a water soluble, low viscosity hydroxyalkylmethyl cellulose and a water dispersible starch and a flavoring agent.

14 Claims, No Drawings

BREATH FRESHENING FILM

BACKGROUND OF THE INVENTION

1. Field of the Invention

This invention relates to a rapidly dissolvable orally consumable film for delivering breath freshening and therapeutic agents to the oral cavity.

2. The Prior Art

Oral malodor is an undesirable condition that affects many people. Malodor of the oral cavity, also known as halitosis or bad breath has been estimated to afflict about 20–90 million people in the United States. To combat oral cavity malodor, the art has developed a variety of products including breath freshening gums, lozenges and mints. The use of these products is not always socially acceptable as they require a sucking or chewing action on the part of the consumer over an extended period of time which can be distracting in a social or business setting.

It is known to the prior art to use consumable films adapted to dissolve in the oral cavity containing flavoring agents for delivering breath freshening agents. For example, WO 00/18365 discloses a breath freshening film adapted to dissolve in a mouth of a consumer comprised of a water soluble polymer such as pullulon or hydroxypropylmethyl cellulose and an essential oil selected from thymol, methyl salicylate, eucalyptol and menthol.

U.S. Pat. No. 4,713,243 discloses a bioadhesive film for delivering therapeutic agents to the oral cavity which is capable of adhering to a wet mucosa surface, composed of a water soluble polymer matrix of 40–95% by weight of a hydroxypropyl cellulose having a molecular weight of about 100,000, 5–60% of a homopolymer of ethylene oxide having a molecular weight from 3,000,000 to 5,000,000, 0–10% of a water-insoluble polymer selected from ethyl cellulose, propyl cellulose, polyethylene and polypropylene, and 10% of a plasticizer, the film having incorporated therein a pharmaceutically effective amount of medicament for the treatment of periodontal disease. The film is flexible when wet so as to be unobtrusive to the user after it has been properly positioned and placed in the mouth.

U.S. Pat. No. 5,354,551 discloses a water soluble film presegmented into dosage units, the film containing conventional toothpaste ingredients and formulated with swellable polymers such as gelatin and corn starch as film forming agents which upon application to the oral cavity slowly disintegrate, thereby releasing an active agent incorporated in the film.

U.S. Pat. No. 6,177,096 discloses a film composition containing therapeutic and/or breath freshening agents for use in the oral cavity prepared from a water soluble polymer such as hydroxypropylmethyl cellulose, hydroxypropylcellulose and a polyalcohol such as glycerol, polyethylene glycol. When applied to the oral cavity, the film exhibits instant wettability followed by rapid dissolution.

Despite the existence in the prior art of rapidly dissolvable orally consumable films, there is still room for improvement in such films, namely the speed with which the film dissolves in the mouth. Unless the film is substantially instantly dissolvable when placed in the mouth, that is within about 30–40 seconds, the undissolved film residue imparts an unacceptable, unpalatable, slimy feel to the palate of the consumer.

SUMMARY OF THE INVENTION

In accordance with the present invention there is provided a rapidly dissolvable, orally consumable film composition for delivering breath freshening agents to the oral cavity, the composition being comprised of a homogeneous mixture of a water soluble, low viscosity hydroxyalkylmethyl cellulose, a water dispersible starch and a flavoring agent.

The hydroxyalkymethyl cellulose serves as a strong film former to give the film the necessary mechanical strength and maintain the integrity of the film at elevated temperature. The starch ingredient increases the stiffness of the film and reduces the curling of the film. The presence in the film of the starch ingredient is also critical to the practice of the present invention for in the absence of the starch, the film tends to curl up after manufacture which is undesirable in the packaging and ultimate use of the film.

Upon administration of the film of the present invention, due to its rapid dissolution, there is provided a burst of breath freshening agent to the oral cavity, without any lingering unpleasant residue on the users palate.

DETAILED DESCRIPTION OF THE INVENTION

The film of the present invention comprises hydroxyalkylmethylcellulose as a film forming agent combined with starch, and a flavoring agent particularly an essential oil as the breath freshening agent. The film can further comprise water, additional film forming agents, plasticizing agents, flavoring agents, antimalodor agents, surfactants, emulsifying agents, coloring agents, sweeteners and fragrances.

In preparing the film according to the present invention, a low viscosity hydroxyalkylmethyl cellulose, a starch ingredient, a breath freshening agent and other film forming ingredients are dissolved in a compatible solvent to form a film forming composition. The hydroxyalkyl cellulose to starch ratio (by weight) may vary from about 1:3 to about 4:1 and preferably about 1:1.5 to about 2.5:1.

The composition is cast on a releasable carrier and dried. The carrier material must have a surface tension which allows the film solution to spread evenly across the intended carrier width without soaking to form a destructive bond between the film and carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely effect the ingredients of which the film is composed.

The film once formed is segmented into dosage units by die-cutting or slitting-and-die-cutting. The segmented film has a strip width and length corresponding to about the size of a postage stamp, generally about 12 to about 30 millimeter in width and about 20 to about 50 millimeters in length. The film has a thickness ranging from about 15 to about 80 micrometers, and preferably about 30 to 60 micrometers.

The film is shaped and sized to be placed in the oral cavity. The film is flexible and adheres to a surface in the mouth, usually the roof of the mouth or the tongue, and quickly dissolves, generally in less than 30–40 seconds.

The film forming agent used in the films according to the present invention is preferably a low viscosity hydropropylmethyl cellulose polymer (HPMC). It is critical to the present invention that the HPMC have a viscosity in the range of about 1 to about 40 millipascal seconds (mPa·s) as determined as a 2% by weight aqueous solution of the HPMC at 20° C. using a Ubbelohde tube viscometer. Preferably the HPMC has a viscosity of about 3 to about 20 mPa·s at 20° C. As will hereinafter be demonstrated, it is critical to the practice of the present invention that a low viscosity hydroxyalkylmethyl cellulose be used in the preparation of the film matrix. At viscosities appreciably higher than about 40 mPa·s, for a given film thickness, the lower the viscosity of a hydroxyalkyl methyl cellulose such as HPMC, the more rapid the dissolution of the film matrix and the burst of breath freshening ingredients.

The hydroxyalkyl methyl cellulose is incorporated in the film composition in amounts ranging from about 10 to about 60% by weight and preferably about 15 to about 40% by weight.

The HPMC polymer is a preferred hydroxyalkylmethyl cellulose polymer and is available commercially from the Dow Chemical Company under the trade designation Methocel E5 Premium LV. Methocel E5 Premium LV is a USP grade, low viscosity HPMC having 29.1% methoxyl groups and 9% hydroxyproxyl group substitution. It is a white or off-white free-flowing dry powder. As a 2 wt % solution in water as measured with a Ubbelohde tube viscometer it has a viscosity of 5.1 mPa·s at 20° C.

Cold water swellable, physically modified and pregelatinized starches are particularly useful as texture modifier to increase the stiffness of the hydroxyalkyl methyl cellulose polymer films of the present invention, as the breath film prepared by HPMC alone, at the thicknesses described for the present invention, tends to curl up after it is cast and dried. To prepare such starch products, the granular starch is cooked in the presence of water and possibly an organic solvent at a temperature not higher than 10° C. higher than the gelatinization temperature. The obtained starch is then dried.

Pregelatinized corn starch is available commercially. A preferred starch is available under the trade designation Cerestar Polar Tex-Instant 12640 from the Cerestar Company. This Cerestar starch is a pregelaterized, stabilized and crosslinked waxy maize starch. It is readily dispersible and swellable in cold water. In its dry form, it is a white free flowing powder with an average particle size no greater than 180 micrometers and 85% of the particles are smaller than 75 micrometers. It has a bulk density of 44 lbs/ft$^3$.

The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor.

The pregelatinized starch is present in the film of the present invention in an amount ranging from about 5 to about 50% by weight and preferably about 10 to about 35% by weight.

Flavor agents that can be used to prepare the breath freshening film of the present invention include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63–258, may be used.

The amount of flavoring agent employed is normally a matter of preference subject to such factors as flavor type, individual flavor, and strength desired. Generally the flavoring is incorporated in the film of the present invention in an amount ranging from about 2.0 to about 10% by weight and preferably about 5 to about 8% by weight.

Sweeteners useful in the practice of the present invention include both natural and artificial sweeteners. Suitable sweetener include water soluble sweetening agents such as monosaccharides, disaccharides and plysaccharides such as xylose, ribose, glucose (dextrose), mannose, glatose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame).

In general, the effective amount of sweetener is utilized to provide the level of sweetness desired for a particular composition, will vary with the sweetener selected. This amount will normally be about 0.01% to about 2% by weight of the composition.

The compositions of the present invention can also contain coloring agents or colorants. The coloring agents are used in amounts effective to produce the desired color and include natural food colors and dyes suitable for food, drug and cosmetic applications. These colorants are known as FD&C dyes and lakes. The materials acceptable for the foregoing spectrum of use are preferably water-soluble, and include FD&C Blue No.2, which is the disodium salt of 5,5-indigotindisulfonic acid. Similarly, the dye known as Green No.3 comprises a 15 triphenylmethane dye and is the monosodium salt of 4-[4-N-ethyl-p-sulfobenzylamino) diphenyl-methylene ]-[1-N-ethy 1-N-sulfonium benzyl)-2, 5-cyclo-hexadienimine ]. A full recitation of all FD&C and D&C dyes and their corresponding chemical structures may be found in the Kirk-Othrner Encyclopedia of Chemical Technology, Volume 5, Pages 857–884, which text is accordingly incorporated herein by reference.

Active breath freshening agents can be incorporated into the film composition of the present invention to form the breath freshening strips of the present invention. The active ingredients include zinc gluconate, zinc citrate and/or alpha ionone. These agents function in masking mouth odor and reducing volatile odor causing bacterial sulfur compounds. These agents may be incorporated in the film composition of the present invention at a concentration of about 0.1 to about 2.0% by weight and preferably about 0.15 to about 0.5% by weight.

The present invention is illustrated by the following examples.

EXAMPLE 1

A breath freshening film was prepared by using the ingredients listed in Table I below. In preparing the film, the HMPC polymer Methocel E5LV having a viscosity of 5.1 mPa·s (2% aqueous solution) was added to deionized water at 23° C., zinc gluconate trihydrate was added and the solution stirred for 5 minutes. To this solution was added the pregelatized starch Cerestar Polar Tex Instant 12640 and stirred vigorously for about one hour until the starch was completely dispersed and a homogeneous mixture was formed. To this mixture was added the dye, FD&C green #3, and mixed for 10 minutes after which the emulsifier polysorbate 80 was added and mixed for an additional 15 minutes. Thereafter spearmint flavor, was thoroughly mixed for an additional 40 minutes to form a slurry emulsion. The weight ratio of HPMC to pregelatinized starch was 1.2. The emulsion was then cast on a polyethylene coated paper at 25° C. and dried at 110° C. to form a solid thin film.

To determine the speed of dissolution of the film in water, the film was floated on a clean and smooth water surface at 5 °C. The thin film (40 um thick, 1.25"×0.875") disintegrated completely in 30 seconds after being placed afloat on a clean and smooth water surface.

The film was evaluated for a breath freshening benefit by in-vitro volatile sulfur compound (VSC) reduction assay. In this assay a known amount of breath film is dissolved in a 3.0 milliliters (ml) of saliva in a glass vial. After incubation at 37° C. overnight, the headspace of the solution is sampled and analyzed for the VSC. The VSC assay results are presented in Table II.

TABLE I

| Ingredients | Wt. % |
| --- | --- |
| Water | 76.71 |
| HPMC | 9.075 |
| Corn Starch (pregelatized) | 7.563 |
| Flavor | 5.85 |
| Polysorbate 80 | 0.35 |
| Zinc gluconate | 0.21 |
| Sucralose | 0.24 |
| FD&C green | 0.002 |

TABLE II

VSC ASSAY OF THE BREATH FILM

| Sample No. | Film Quantity in Saliva (mg/3 mL) | VSC Reduction (%) |
| --- | --- | --- |
| 1 | 0 | 0 |
| 2 | 10 | 5 |
| 3 | 20 | 11 |
| 4 | 30 | 17 |

The VSC results recorded in Table II demonstrate that the breath freshening benefit of the film is proportional to the amount of film exposure.

EXAMPLE II

Three different breath films were prepared following the procedure of Example 1 according to the general formula of Table III. The three films shared the same formula except for the type of Methocel HPMC polymer used. Film A was prepared using Methocel E5LV having a viscosity of 5.1 mPa·s. For purposes of comparison, Films B and C were prepared using HPMC polymers Methocel F50 and Methocel E4M having a viscosities of 50 and 4000 mPa·s respectively. The dispersion rates of the three different films were tested using the same surface-floating procedure as used in Example I and the results are listed in Table IV.

TABLE III

GENERAL FORMULA OF FILMS A, B AND C

| Ingredients | Weight % |
| --- | --- |
| Methocel | 6.85 |
| Cerestar Polar Tex Instant 12640 | 5.70 |
| Tween 80 | 0.50 |
| Propylene glycol | 4.00 |
| Sucralose | 0.125 |
| Zinc gluconate | 0.173 |
| FD&C Green #3 | 0.002 |
| Spearmint flavor | 6.0 |
| Cooling agent | 0.50 |
| Deoinized water | 76.05 |

TABLE IV

DISPERSION RATES OF FILM A, B AND C

| | Film Base | | | | Film | |
| --- | --- | --- | --- | --- | --- | --- |
| Formula | Methocel | HPMC Viscosity (mPa·s) | Starch | Methocel/ Starch ratio by wt. | Film Thickness (micrometers) | Dispersion rate (seconds) |
| A | E5 | 5.1 | Cerestar | 1.2 | 42 | 40 |
| B | F50 | 50 | Cerestar | 1.2 | 42 | 72 |
| C | E4M | 4000 | Cerestar | 1.2 | 39 | 205 |

The results recorded in Table IV indicate that films prepared using viscosities of 50 mPa·s or more dissolve appreciably slower than a film prepared using a HPMC having a viscosity less than 50 mPa·s.

What is claimed is:

1. An orally consumable film composition for delivering breath freshening agents to the oral cavity which is rapidly dissolvable in the oral cavity, the composition being comprised of a homogeneous mixture of (1) a water soluble, low viscosity hydroxyalkylmethyl cellulose, the viscosity being in the range of 1 to about 40 mPa·s as determined as a 2% by weight aqueous solution at 20° C. using a Ubbelohde tube viscometer, (2) a water dispersible pregelatized starch, and (3) a flavoring agent.

2. The film composition of claim 1 wherein the hydroxyalkyl methyl cellulose is hydroxypropyl methyl cellulose.

3. The film composition of claim 1 wherein the viscosity of the hydroxyalkyl methyl cellulose is in the range of about 3 to about 30 mPa·s.

4. The film composition of claim 1 wherein the hydroxyalkyl methyl cellulose is present at a concentration of about 10 to about 60% by weight.

5. The film composition of claim 1 wherein the starch is present in the film in an amount ranging from about 5 to about 50% by weight.

6. The film composition of claim 1 wherein the weight ratio of hydroxyalkyl methyl cellulose to starch is in the range of about 1:3 to about 4:1.

7. The film composition of claim 1 wherein the weight ratio of hydroxyalkyl methyl cellulose to starch is in the range of about 1:1.5 to about 2:5.1.

8. A method for delivering a breath freshening agent to the oral cavity which comprises preparing an orally consumable film composition which is rapidly dissolvable in the oral cavity, the composition being comprised of (1) a homogeneous mixture of a water soluble, low viscosity hydroxyalkylmethyl cellulose, the viscosity being in the range of 1 to about 40 mPa·s as determined as a 2% by weight aqueous solution at 20° C. using a Ubbelohole tube viscometer, (2) a water dispersible starch, and (3) a flavoring agent.

9. The method of claim 8 wherein the hydroxyalkyl methyl cellulose is hydroxypropyl methyl cellulose.

10. The method of claim 8 wherein the viscosity of the hydroxyalkyl methyl cellulose is in the range of about 3 to about 30 mPa·s.

11. The method of claim 8 wherein the hydroxyalkyl methyl cellulose is present at a concentration of about 10 to about 60% by weight.

12. The method of claim 8 wherein the starch is present in the film in an amount ranging from about 5 to about 50% by weight.

13. The method of claim 8 wherein the weight ration of hydroxyalkyl methyl cellulose to starch is in the range of about 1:3 to about 4:1.

14. The method of claim 8 wherein the weight ratio of hydroxyalkyl methyl cellulose to starch is in the range of about 1:1.5 to abut 2:5.1.

* * * * *